(12) United States Patent
Galavotti et al.

(10) Patent No.: US 10,563,646 B2
(45) Date of Patent: Feb. 18, 2020

(54) PERISTALTIC PUMP TUBE

(75) Inventors: Francesca Galavotti, Medolla (IT);
Carlo Giannella, Mirandola (IT)

(73) Assignee: Gambro Lundia AB, Lund (SE)

( * ) Notice: Subject to any disclaimer, the term of this patent is extended or adjusted under 35 U.S.C. 154(b) by 1401 days.

(21) Appl. No.: 11/662,020

(22) PCT Filed: Jul. 6, 2005

(86) PCT No.: PCT/IB2005/001919
§ 371 (c)(1),
(2), (4) Date: Mar. 5, 2007

(87) PCT Pub. No.: WO2006/027647
PCT Pub. Date: Mar. 16, 2006

(65) Prior Publication Data
US 2008/0188789 A1 Aug. 7, 2008

(30) Foreign Application Priority Data

Sep. 6, 2004 (IT) .............................. MO2004A0223

(51) Int. Cl.
*A61M 37/00* (2006.01)
*F04B 43/00* (2006.01)
(Continued)

(52) U.S. Cl.
CPC .......... *F04B 43/0072* (2013.01); *A61M 37/00* (2013.01); *B29C 48/793* (2019.02); *B29C 48/832* (2019.02)

(58) Field of Classification Search
CPC ......... A61M 37/00; F04B 43/08; F04B 43/12; F04B 45/06; F04B 43/00; F04C 21/00; F16L 9/18
(Continued)

(56) References Cited

U.S. PATENT DOCUMENTS 3,176,622 A * 4/1965 Pfeiffer .................... 417/477.12
4,012,177 A 3/1977 Yakich
(Continued)

FOREIGN PATENT DOCUMENTS

DE      4317741 A1 * 1/1994
DE      43 17 741 A1 12/1994
(Continued)

OTHER PUBLICATIONS

The American Heritage Dictionary of the English Language, Fourth Edittion, 2000.*
(Continued)

*Primary Examiner* — Tatyana Zalukaeva
*Assistant Examiner* — Ilya Y Treyger
(74) *Attorney, Agent, or Firm* — K&L Gates LLP

(57) ABSTRACT

A tube for a peristaltic pump comprises an elastically deformable tubular body (2) made from a PVC composition containing: 100 phr of a PVC resin having a K value, measured according to standard ISO 1628-2, of not less than 85, from 40 to 100 phr of DEHA plasticizer, from 0.05 to 1.0 phr of lubricant, from 0.3 to 15.0 phr of stabilizer and co-stabilizer. The deformable tube, which is usefully employed for liquid transport in a dialysis apparatus, enables a high level of fluid transport efficiency to be maintained, even after many hours of peristaltic pump operation.

20 Claims, 3 Drawing Sheets

(51) Int. Cl.
*B29C 48/793* (2019.01)
*B29C 48/80* (2019.01)
*F04B 43/08* (2006.01)
*F04B 45/06* (2006.01)

(58) Field of Classification Search
USPC ........ 604/4.01, 6.11; 417/474–478, 479–481
See application file for complete search history.

(56) References Cited

U.S. PATENT DOCUMENTS

| | | | |
|---|---|---|---|
| 4,080,113 A | | 3/1978 | Legeay, nee Lechat et al. |
| 4,177,182 A | | 12/1979 | Ichikawa et al. |
| 4,296,017 A | * | 10/1981 | Weissgerber et al. ........ 524/139 |
| 4,299,256 A | | 11/1981 | Bacehowski et al. |
| 4,557,959 A | | 12/1985 | Kuehlein et al. |
| 4,577,998 A | * | 3/1986 | Dorrn ............................ 405/45 |
| 4,581,029 A | | 4/1986 | Joh |
| 4,612,340 A | | 9/1986 | Ohachi |
| 4,705,464 A | * | 11/1987 | Arimond .................... 417/477.7 |
| 4,749,757 A | * | 6/1988 | Schram et al. ................. 526/83 |
| 5,061,365 A | | 10/1991 | Utterberg |
| 5,067,879 A | | 11/1991 | Carpenter |
| 5,088,522 A | | 2/1992 | Rath et al. |
| 5,215,450 A | | 6/1993 | Tamari |
| 5,242,279 A | | 9/1993 | Knuth |
| 5,721,024 A | | 2/1998 | Carmen et al. |
| 5,810,786 A | * | 9/1998 | Jackson et al. ............... 604/265 |
| 5,955,519 A | | 9/1999 | Neri |
| 5,965,198 A | | 10/1999 | Plusquellec et al. |
| 6,187,400 B1 | * | 2/2001 | Woo et al. .................... 428/36.6 |
| 6,431,219 B1 | * | 8/2002 | Redler et al. .................. 138/137 |
| 6,440,095 B1 | | 8/2002 | Utterberg |
| 6,731,216 B2 | | 5/2004 | Ho et al. |
| 2002/0068786 A1 | | 6/2002 | Graefe et al. |
| 2003/0036719 A1 | * | 2/2003 | Giacomelli et al. ......... 604/5.04 |

FOREIGN PATENT DOCUMENTS

| | | |
|---|---|---|
| DE | 43 17 741 C2 | 12/1994 |
| DE | 4317741 A1 | 12/1994 |
| DE | 44 25 240 A1 | 1/1996 |
| DE | 44 25 240 C2 | 1/1996 |
| DE | 692 07 013 T2 | 5/1996 |
| DE | 20312108 * | 11/2003 |
| DE | 102 39 738 A1 | 3/2004 |
| EP | 0 086 512 B1 | 8/1983 |
| EP | 0 388 596 A1 | 9/1990 |
| EP | 0 496 547 B1 | 7/1992 |
| EP | 0 663 216 A2 | 7/1995 |
| EP | 0 842 220 B1 | 5/1998 |
| EP | 1 140 257 B1 | 10/2001 |
| EP | 1 393 759 A1 | 3/2004 |
| EP | 1 402 885 A1 | 3/2004 |
| WO | WO 89/04923 | 6/1989 |
| WO | WO 95/11383 | 4/1995 |

OTHER PUBLICATIONS

Vinnolit (Product Information). 2004.*
Vinnolit GMBH & Co. KG, "Vinnolit S 4099 Product Information", Jan. 2004, 2 pages.
Michaeli Walter, "Einführung in die Kunststoffverarbeitung (Introduction into plastics processing)", Carl Hanser Verlag, 4. Ed., 1999, 29 pages, including pp. 74-100.
Saechtling, "Kunststofftaschenbuch (Handbook of plastics)", Carl Hanser Verlag, 28. Ed., 2001, 12 pages, including pp. 444-463.
Saechtling, "Kunststofftaschenbuch (Handbook of plastics)", Carl Hanser Verlag, 21. Ed., 1979, 5 pages.
DIN, "ISO 1628-2", Second edition, Dec. 1, 1998, 19 pages.
DIN, "EN ISO 1628-2", Nov. 1999, 15 pages.
DIN, "EN ISO 1628-1", Oct. 1998, 11 pages.
DIN, "53726", Sep. 1983, 5 pages.
Rehau AG & Co., "Invoice No. R80236443", May 5, 2004, 1 page.
Rehau AG & Co., "Technische Lieferbedingung V-T 36/22 (Technical Delivery Conditions V-T 36/22)", Jul. 29, 1999, 2 pages.
Rehau AG & Co., "Technical Drawing REHAU high pressure tube", Jul. 29, 1999, 2 pages.
Rehau AG & Co., "Email of Mr. Martin Heinlein", Jan. 29, 2010, 4 pages.
Franz (Ed.), "Dialyse fur Pflegeberufe (Dialysis for nursing professions)", Georg Thieme Verlag, 2. Ed., 1996, 3 pages.
Rehau, "Product Brochure", Feb. 1992, 4 pages.
Rehau, "Product Brochure RAUMEDIC ECC", Jul. 1992, 8 pages.
Falbe, Regitz (Eds.), "Rompp Lexikon Chemie (Rompp Lexicon of Chemistry)", Georg Thieme Verlag, 5. vol. 10. Ed., 1998, 3 pages, including p. 4075.
PCE-Group, "Bedienungsanleitung des Hartemessers PCE-DX-AS Shore A (Operating manual for hardness tester PCE-DX-AS Shore A)", at least as early as Mar. 4, 2007, 1 page.
Gachter, Muller (Eds.), "Taschenbuch der Kuststoffadditive (Handbook of Plastics Additives)", Carl Hanser Verlag, 1 Ed., 1990, 18 pages.
Falbe, Regitz (Eds.), "Rompp Lexikon Chemie (Rompp Lexicon of Chemistry)", Georg Thieme Verlag, 2. vol. 10. Ed., 1997, 3 pages, including p. 1553.
Avokal and Heller, "Hardcopy of Avokal and Heller Webpage", at least as early as Mar. 4, 2007, 3 pages.

* cited by examiner

FIG 1
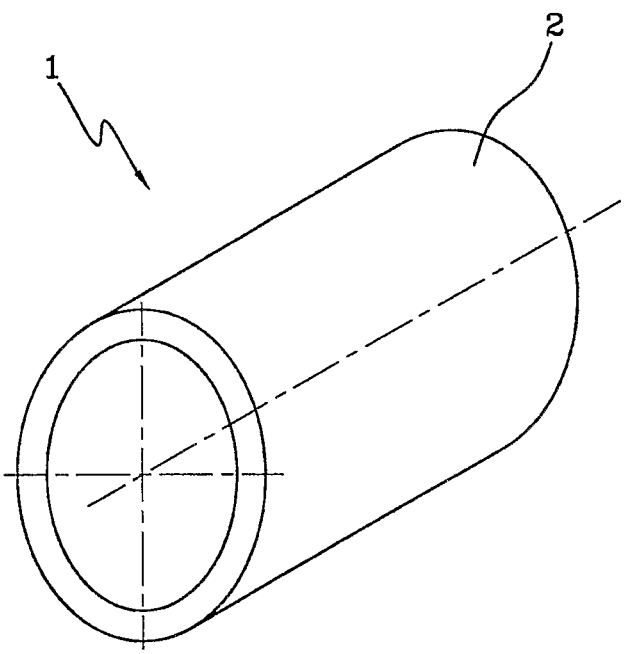
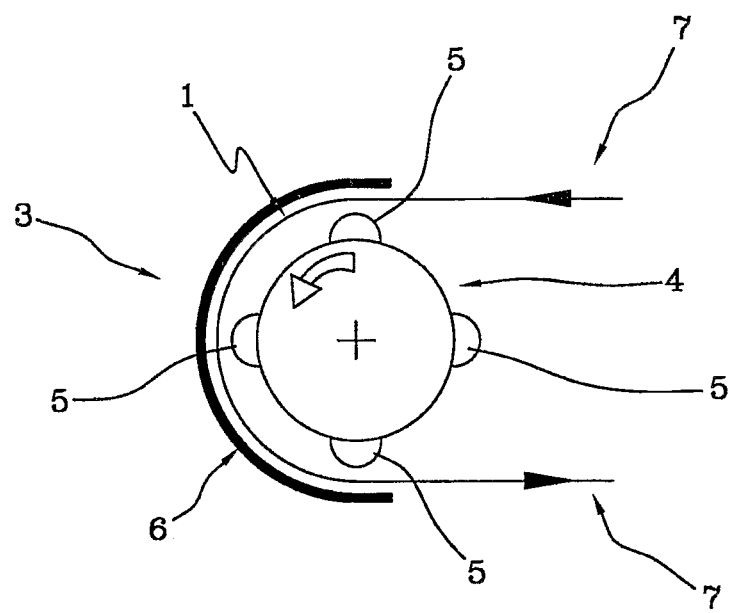
FIG 2

PERISTALTIC PUMP TUBE

BACKGROUND OF THE INVENTION

The invention relates to a tube for a peristaltic pump.

Specifically, though not exclusively, the invention can be usefully employed for transport of a liquid, for example a corporeal fluid (blood) and/or a medical fluid, in a medical apparatus, in particular in an apparatus for extracorporeal blood treatment, such as for example a dialysis apparatus.

The use of deformable-tube peristaltic pumps for transport of liquids is known and widespread. Some examples of deformable tubes used in peristaltic pumps are shown in patent publications U.S. Pat. No. 4,080,113, WO 89/04923, WO 95/11383, U.S. Pat. No. 5,088,522, EP 0 388 596, U.S. Pat. No. 5,242,279. In a peristaltic pump the tube, which is elastically deformable and contains the fluid to be transported, is squeezed by a mobile device (for example a rotor having at a periphery thereof two or more squeezing rollers) in a zone which progressively advances along the length of the tube so as to push the fluid forward. The tube has elastic return which enables the squeezing-pushing action to be repeated cyclically.

One of the problems of known-type peristaltic pumps consists in the fact that the deformable tube, generally made of a relatively soft plastic material, such as for example plasticated PVC, is prone to considerable wear by effect of the squeezing and sliding pressure it is subjected to by the mobile device, with a consequent degrading of its characteristics, especially its mechanical characteristics, for example its elastic return capacity. This has a considerable effect on the efficiency of the peristaltic pump over a long use time, causing the fluid flow along the tube to diminish progressively even where the squeezing-pushing action stays the same.

This leads to various drawbacks.

Firstly, the progressive drop in performance of the peristaltic pump considerably limits the work time of the deformable tube. In applications where it is possible to do so, the worn deformable tube is periodically replaced. In other applications, for example in extracorporeal blood circuits, in which the deformable tube (also known as the pump segment) cannot be easily substituted in isolation from the rest of the circuit; the whole circuit has to be changed too, with consequent complications and a considerable impact on costs.

Secondly, the variability over time of the peristaltic pump efficiency leads to a certain imprecision in the determination of the fluid flow, with a consequent need, in some cases, to set up elaborate flow control and regulation systems, especially in applications where the precision of the flow measure is essential, such as for example in medical apparatus in general, and in dialysis apparatus in particular, where control of the ultrafiltration flow and/or the infusion flow must be very precisely performed.

SUMMARY OF THE INVENTION

The main aim of the present invention is to provide a tube for a peristaltic pump which is able to obviate the above limitations and drawbacks in the prior art.

An advantage of the invention is that it provides a deformable tube which, used in a peristaltic pump for transport of a fluid, maintains a high level of efficiency of fluid transport, i.e. a high flow rate in relation to the squeeze-and-push action, even after many hours of operation.

A further advantage is to make available a tube which is simple and economical to manufacture.

A further aim of the invention is to realise a fluid circuit for medical use, such as for example an extracorporeal blood circuit or a sterile fluid circuit, which is provided with a pump segment that is couplable to a peristaltic pump and which is also able to work, together with the pump, with a high-level performance for a long time.

In a specific embodiment of the invention, the deformable tube is realized with a PVC resin-based material having a K value, measured according to ISO 1628-2, which is greater than 85, where the K value represents, as is known, an indicative measure of the PVC molecular weight. It has been unexpectedly found that by using a PVC resin of this type for production of deformable tubes for peristaltic pumps, the wearing of the deformable tube by the squeeze-push action typical of peristaltic pumps is considerably reduced. It has emerged that the peristaltic pump (i.e. the fluid flow rate in relation to the power of the peristaltic pump) undergoes a decidedly lower drop in performance in comparison to deformable tubes used up to now in peristaltic pumps, where the K value is less than 85.

In a specific embodiment of the invention, the PVC resin used for manufacturing the deformable tube has a K value of more than 95, more specifically comprised between 97 and 105.

In a specific embodiment of the invention, the quantity of plasticizer used in the PVC composition is comprised between 40 and 100 phr, i.e. parts in weight of plasticizer per 100 parts in weight of PVC resin. It has been found that the above range of plasticizer percentage values favours the obtaining of a deformable tube for peristaltic pumps offering excellent performance, in relation to the limitations in the drop in pump flow rate by effect of wear in the tube due essentially to the squeeze-push action of the pump on the tube.

In a specific embodiment of the invention, the deformable tube is sterilized by irradiation using penetrating rays such as for example beta/gamma rays. The resistance to penetrating rays of the PVC composition of the present invention is high.

Further characteristics and advantages of the present invention will better emerge from the detailed description that follows, of at least one embodiment of the invention, illustrated purely by way of non-limiting example in the following figures of the drawings.

BRIEF DESCRIPTION OF THE DRAWINGS

FIG. 1 shows a sectioned tract of a tube realised in accordance with the present invention.

FIG. 2 is a schematic view of a peristaltic pump comprising the tube of FIG. 1.

DETAILED DESCRIPTION

Figure 3:
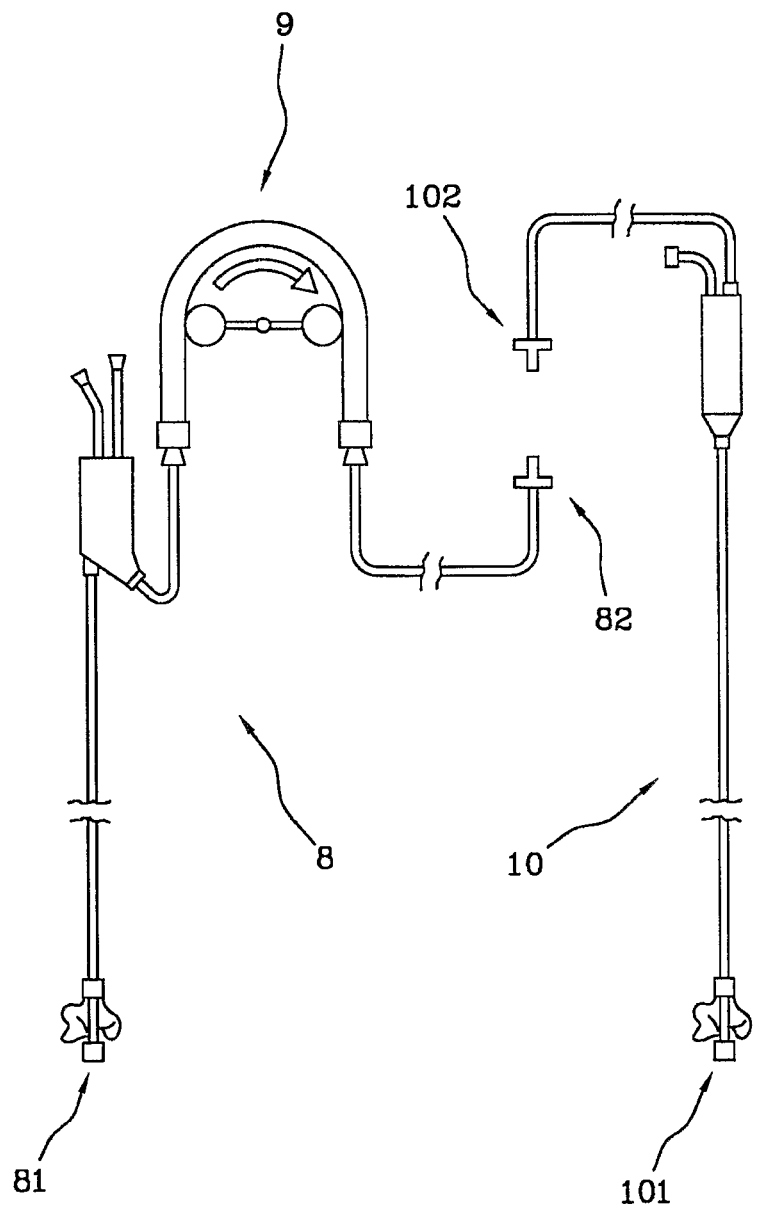
FIG. 3 illustrates a dialysis set comprising the tube of FIG. 1.

With reference to FIG. 1, 1 denotes in its entirety a tube for a peristaltic pump, comprising an elongate tubular body 2 which is elastically deformable by squeezing, and which is flexible. The tubular body 2 has a cylindrical, smooth and continuous surface, and an internal surface which is also cylindrical, smooth and continuous, has a thickness of about 0.8 millimetre and an internal diameter of about 3.2 millimetres. The tubular body 2 is made from a material containing at least a vinyl chloride resin and an least a plasticizer. The tubular body 2 is made whole, in a single layer of the said material.

The PVC resin used has a K value, measured according to ISO 1628-2 standards, of not less than 85. More specifically, the resin has a K value, measured according to ISO 1628-2, of not less than 95. In laboratory testing, the results of which will be described herein below, a PVC resin was used that had a rated K value of 100. The use of polymerized vinyl chloride with K above 95 is known, for example from DE 4317741, for producing PVC formulations used in the thermoplastic manufacturing of soft elasticized products by extrusion, pressing, calendering or sintering.

The material of the tubular body 2 contains a quantity of plasticizer which is not above 100 phr, where phr means parts in weight per hundred parts of resin. The plasticizer content is also above 40 phr. In greater detail, the content in weight of plasticizer in the tubular body 2 is comprised between 50 and 80 phr. In a specific embodiment which has been subjected to laboratory testing, the material of the tubular body contains about 75.5 phr of plasticizer. In the embodiment the plasticizer used is a monomer.

The plasticizer comprises, in particular, a derivative of adipic acid. More specifically, the derivative can be an alkyl ester of adipic acid, such as for example di-2-ethyl-hexyladipate, commonly known as DOA or DEHA. The use of DEHA as a plasticizer for PVC compositions in the manufacturing of bio-compatible articles is known, for example from patent publication U.S. Pat. No. 5,955,519.

A formulation of the material used for realising the tubular body 2 is the following:
   100 phr of PVC resin;
   from 40 to 100 phr of plasticizer;
   from 0.05 to 1.0 phr of one or more lubricants;
   from 0.1 to 5.0 phr of one or more stablizers;
   from 0.2 to 10.0 phr of one or more co-stabilizers.

Any type of lubricant suitable for PVC mixtures can be used.

Among the usable stabilizers are Ca/Zn stabilizers, based on calcium and zinc.

A usable co-stabilizer is, for example, epoxy soya oil (ESO), although other types of known co-stabilizers suitable for PVC can be used.

The deformable tube, especially in the case of medical use, can be sterilized using any known sterilization process, such as for example using penetrating beta/gamma rays or ethylene oxide. The above-illustrated PVC composition exhibits good resistance to penetrating rays.

FIG. 2 schematically shows a peristaltic pump 3 for transport of a fluid, using a deformable tube 1 such as the one described above. The peristaltic pump 3, which in the embodiment is rotary, comprises a rotor 4 provided with a plurality of squeezing rollers 5, a stator 6 external of the rotor, and a deformable tube arranged between the rotor 5 and the stator 6. The deformable tube is inserted in a fluid transport line 7 which can be, for example, a line for extracorporeal blood transport, or an infusion line for a medical fluid, or a dialysis fluid supply line to a dialyzer filter, or an out-flowing discharge fluid drainage line from a blood treatment unit, and so on.

FIG. 3 shows, schematically, a set for fluid transport in an extracorporeal blood treatment; more specifically it shows a set for extracorporeal blood transport for a dialysis treatment. The set comprises an arterial line 8, provided with a pump segment 9 realized by the tube of the present invention, and a venous line 10, each provided with one end, respectively 81 and 101, for connection to the blood circulation system of a patient, and another end, respectively 82 and 102, for connection to a blood treatment unit (of known type and not illustrated).

The tube of the invention is for coupling a peristaltic pump of the type which is operatively associated, in particular, to apparatus for extracorporeal blood treatment, such as for example apparatus predisposed to perform one or more of the following treatments: hemodialysis, hemofiltration, therapeutic plasma exchange, hemodiafiltration, pure ultrafiltration.

These apparatus can be of a type suitable for intensive treatment of kidney failure, or of a type suitable for periodic treatments.

The tube of the invention is further couplable with peristaltic pumps suitable for other medical uses such as, for example, apparatus for infusion of a medical fluid into a patient where there is the presence of at least one peristaltic pump.

EXAMPLE

A deformable tube for a peristaltic pump was manufactured using the following PVC formulation:
   100 phr of PVC resin with K of about 100, commercially known as Vinnolit® S 4099;
   75.5 phr of DEHA plasticizer;
   5.0 phr of ESO co-stabilizer;
   1.2 phr Ca/Zn stabilizer;
   0.2 phr of lubricant.

The tube was made by extrusion of a blend of the above ingredients. The blend was heated to a temperature of between 120 and 150° C. to enable good blending of the various components, after which the resulting dry blend was used for extrusion of the tube. Extrusion temperature for the deformable tube was about 160-180° C. Tube dimensions are those of the tube 1 of FIG. 1. The extruded tube was then sterilized using ethylene oxide and applied together with a rotary peristaltic pump of a dialysis machine for various operational hours.

Figure 4:
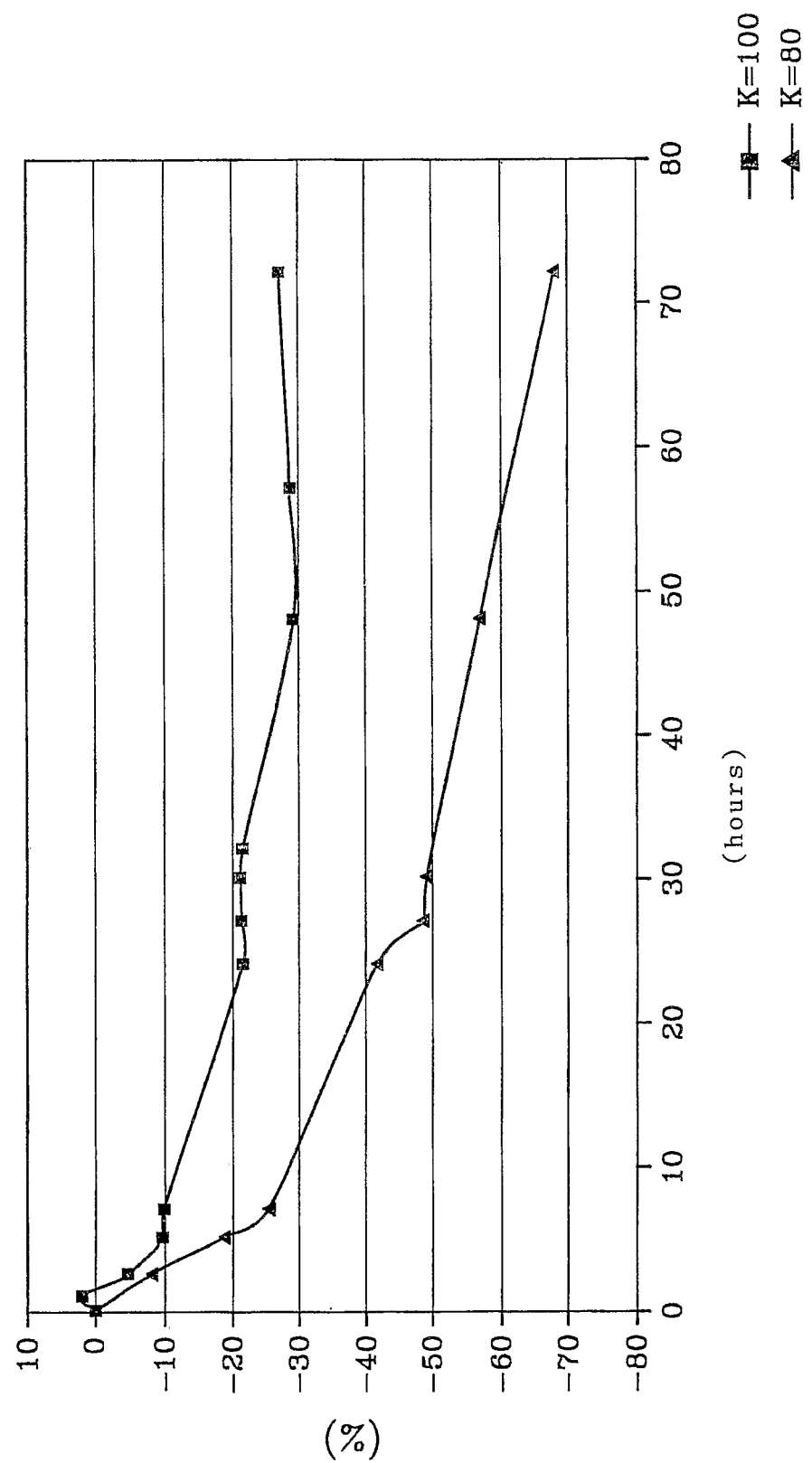
FIG. 4 is a diagram comparing the percentage drop in flow rate in a peristaltic pump over a period of time, for a deformable tube of the invention and for a deformable tube of another type.

The diagram of FIG. 4 shows, on the horizontal axis, the operational time expressed in hours, and on the vertical axis the drop in the test fluid flow rate through the peristaltic pump, expressed in percentage terms with respect to the initial flow rate with the tube when not in a worn state.

The diagram of FIG. 4 includes an indication of the drop in flow rate over a time period, with the peristaltic pump rotor speed kept at a constant rate, of the deformable tube made according to the above description (PVC with K=100). In a second line the drop in flow rate is indicated at the same rotor speed and the same pressure $P_{in}$ at the pump inlet ($P_{in}$=−200 mmHg), using a tube of the same dimensions as the above, but made using a PVC composition in which the PVC resin is about K=80.

It has been demonstrated, then, that thanks to the tube made according to the present invention, the drop in flow rate caused by tube wear is considerable reduced.

More specifically, the above improvement is particularly evident in use with peristaltic pumps with deformable tubes, where, during use, the negative pressure at pump inlet $P_{in}$ is less than about −20 mmHg.

The invention claimed is:

1. A tube for a peristaltic pump, comprising:
   an elastically deformable tubular body, made of a material containing at least a vinyl chloride resin and at least a plasticizer comprising a derivative of adipic acid, the resin having a K value of more than 100 and no more than 105 measured according to standard ISO 1628-2, and the tubular body being made entirely of a single layer of the material.

2. The tube of claim 1, wherein said material contains a quantity of said plasticizer which is comprised between 50 and 80 phr.

3. The tube of claim 1, wherein said plasticizer is a monomer.

4. The tube of claim 1, wherein said derivative is an alkyl ester.

5. The tube of claim 4, wherein said alkyl ester is DEHA.

6. The tube of claim 1, wherein said material contains: 100 phr of said PVC resin; from 40 to 100 phr of said plasticizer; from 0.05 to 1.0 phr of one or more lubricants; from 0.3 to 15.0 phr of one or more stabilizers and co-stabilizers.

7. A set for fluid transport in an extracorporeal blood treatment, comprising at least one tract which is provided with a tube for a peristaltic pump according to claim 1.

8. An apparatus for extracorporeal blood treatment comprising at least a peristaltic pump and a set for fluid transport, the set being realized according to claim 7.

9. The apparatus of claim 8, having a structure configured for performing one or more of following treatments: hemodialysis, hemofiltration, hemodiafiltration, pure ultrafiltration, therapeutic plasma exchange.

10. A blood line comprising at least a first end connector for connection to a patient, at least a second end connector for connection to a blood treatment device, and at least a tract provided with a tube for a peristaltic pump, wherein said tube is made according to claim 1.

11. A use of a tube, made according to claim 1, comprising the step of coupling the tube with a peristaltic pump for fluid transport.

12. A use of a material for manufacturing a deformable tube comprising the step of:
making a deformable tube entirely of a single layer of a material containing at least a vinyl chloride resin and at least a plasticizer comprising a derivative of adipic acid, the resin having a K value of more than 100 and no more than 105 measured according to standard ISO 1628-2; and
coupling the tube with a peristaltic pump for fluid transport, thereby reducing a drop in fluid flow rate following tube wear.

13. A use of a material containing: 100 phr of at least one vinyl chloride resin having a K value, measured in accordance with standard ISO 1628-2, of more than 100 and no more than 105; and a quantity of less than 100 phr of at least a plasticizer comprising a derivative of adipic acid; comprising the step of:
manufacturing a deformable tube entirely of a single layer of the material; and
coupling the tube with a peristaltic pump for fluid transport, thereby limiting a drop of fluid flow rate of the peristaltic pump following wearing of the tube.

14. A process for manufacturing a deformable tube by extrusion, comprising stages of:
preparing a blend containing 100 phr of a vinyl chloride resin, and between 40 and 100 phr of at least a plasticizer comprising a derivative of adipic acid, the resin having a K value, measured according to standard ISO 1628-2, of more than 100 and no more than 105;
heating the blend to a temperature comprised between 120° C. and 150° C.; and
extruding the deformable tube from the blend at a temperature comprised between 160° C. and 180° C. entirely of a single layer of the material.

15. The process of claim 14, wherein said deformable tube is sterilized by irradiation with penetrating rays.

16. A tube for a peristaltic pump, comprising:
an elastically deformable tubular body, made of a material containing at least a vinyl chloride resin and at least a plasticizer comprising a derivative of adipic acid, the resin having a K value of not less than 85 measured according to standard ISO 1628-2, the material containing a quantity of said plasticizer which is not above 100 phr, wherein phr means parts by weight per hundred parts by weight of resin, and the tubular body being made entirely of a single layer of the material.

17. A tube for a peristaltic pump, comprising:
an elastically deformable tubular body, made of a material containing at least a vinyl chloride resin and at least a plasticizer comprising a derivative of adipic acid, the resin having a K value of more than 100 measured according to standard ISO 1628-2, and the tubular body being made entirely of a single layer of the material.

18. The tube of claim 1, wherein said material contains a quantity of said plasticizer which is not above 100 phr, wherein phr means parts by weight per hundred parts by weight of resin.

19. The tube of claim 1, wherein said material contains a quantity of said plasticizer which is above 40 phr.

20. The tube of claim 16, wherein said material contains a quantity of said plasticizer which is above 40 phr.

\* \* \* \* \*